United States Patent
Tanke

(10) Patent No.: US 6,890,569 B1
(45) Date of Patent: May 10, 2005

(54) RESTORATIVE TEA SYSTEM AND ASSOCIATED METHOD

(76) Inventor: Ann M. Tanke, 3360 Pinecrest Dr., Helena, MT (US) 59602

(*) Notice: Subject to any disclaimer, the term of this patent is extended or adjusted under 35 U.S.C. 154(b) by 198 days.

(21) Appl. No.: 10/273,876

(22) Filed: Oct. 18, 2002

(51) Int. Cl.$^7$ ................................................ A01N 65/00
(52) U.S. Cl. ........................ 424/769; 424/725; 514/825; 514/923
(58) Field of Search ................................ 424/725, 769; 514/825, 923

(56) References Cited

U.S. PATENT DOCUMENTS

| | | | | |
|---|---|---|---|---|
| 4,569,839 A | * | 2/1986 | Grollier et al. | ............... 424/74 |
| 5,869,540 A | * | 2/1999 | Smith | .......................... 514/783 |
| 5,908,628 A | * | 6/1999 | Hou | ............................ 424/735 |
| 6,576,270 B2 | * | 6/2003 | Leko | ........................... 424/733 |
| 2002/0122835 A1 | * | 9/2002 | Bucci et al. | ................. 424/729 |

FOREIGN PATENT DOCUMENTS

| | | | |
|---|---|---|---|
| DE | 29911850 | * | 11/1999 |
| RU | 2052255 | * | 1/1996 |

* cited by examiner

*Primary Examiner*—Christopher R. Tate
(74) *Attorney, Agent, or Firm*—Edward P. Dutkiewicz

(57) ABSTRACT

A restorative tea system and method of brewing a tea of one part White Willow bark, one part German Chamomile, one part Parsley, one part Nettles leaf, and one part primula veris.

4 Claims, No Drawings

RESTORATIVE TEA SYSTEM AND ASSOCIATED METHOD

BACKGROUND OF THE INVENTION

1. Field of the Invention the present invention relates to a restorative tea system and associated method and more particularly pertains to combating arthritis and other maladies.

2. Description of the Prior Art

The use of teas and tea regimens is known in the prior art. More specifically, teas and tea regimens previously devised and utilized for the purpose of combating maladies through known methods and recipes consist basically of familiar, expected, and obvious structural configurations, notwithstanding the myriad of designs encompassed by the crowded prior art which has been developed for the fulfillment of countless objectives and requirements.

While these devices fulfill their respective, particular objectives and requirements, the aforementioned patents do not describe restorative tea system and associated method that allows combating arthritis and other maladies.

In this respect, the restorative tea system and associated method according to the present invention substantially departs from the conventional concepts and designs of the prior art, and in doing so provides an apparatus primarily developed for the purpose of combating arthritis and other maladies.

Therefore, it can be appreciated that there exists a continuing need for a new and improved restorative tea system and associated method which can be used for combating arthritis and other maladies. In this regard, the present invention substantially fulfills this need.

SUMMARY OF THE INVENTION

In view of the foregoing disadvantages inherent in the known types of teas and tea regimens now present in the prior art, the present invention provides an improved restorative tea system and associated method. As such, the general purpose of the present invention, which will be described subsequently in greater detail, is to provide a new and improved restorative tea system and associated method and method which has all the advantages of the prior art and none of the disadvantages.

To attain this, the present invention essentially comprises a restorative tea system and associated method to combat arthritis and other maladies. The restorative tea is comprised of two quarts of heated water; four drams of dried White Willow bark; four drams of dried German Chamomile; four drams of dried Parsley; four drams of dried Nettles leaf; and four drams of dried Cowslip also known as primula veris. The method of brewing the restorative tea for combating arthritis and other maladies includes the steps of providing two quarts of water, providing four drams of dried White Willow bark, providing four drams of dried German Chamomile, providing four drams of dried Parsley, providing four drams of dried Nettles leaf, providing four drams of dried Cowslip, bring the two quarts of water to a boil, removing the two quarts of water from heat, adding the four drams of White Willow bark, adding the four drams of German Chamomile, adding the four drams of Parsley, adding the four drams of Nettles leaf, adding the four drams of Cowslip thus forming a mixture, stirring the mixture, covering the mixture tightly, allowing the mixture to steep for ten minutes, uncovering the mixture, stirring the mixture, covering the mixture tightly, allowing the mixture to steep for ten minutes, uncovering the mixture, straining the mixture into a drinking receptacle, allowing the mixture to cool, refrigerating the mixture, drinking 8 ounces of the mixture in the morning and evening and repeating twice a day drinking for six to eight weeks, and if symptoms persist continuing the drinking step for another six to eight weeks.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved restorative tea system and associated method which has all of the advantages of the prior art teas and tea regimens and none of the disadvantages.

it is another object of the present invention to provide a new and improved restorative tea system and associated method which may be easily and efficiently prepared and marketed.

An even further object of the present invention is to provide a new and improved restorative tea system and associated method which is susceptible of a low cost of preparation with regard to both materials and labor, and which accordingly is then susceptible of low prices of sale to the consuming public, thereby making such restorative tea system and associated method economically available to the buying public.

Even still another object of the present invention is to provide a restorative tea system and associated method for combating arthritis and other maladies.

Lastly, it is an object of the present invention to provide a new and improved restorative tea system and method of brewing a tea of one part White Willow bark, one part German Chamomile, one part Parsley, one part Nettles leaf, and one part primula veris.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

DESCRIPTION OF THE PREFERRED EMBODIMENT

The present invention is a restorative tea system and associated method to combat arthritis and other maladies.

The restorative tea is comprised of two quarts of heated water; four drams of dried White Willow bark; four drams of dried German Chamomile; four drams of dried Parsley; four drams of dried Nettles leaf; and four drams of dried Cowslip also known as primula veris. The method of brewing the restorative tea for combating arthritis and other maladies includes the steps of providing two quarts of water, providing four drams of dried White Willow bark, providing four drams of dried German Chamomile, providing four drams of dried Parsley, providing four drams of dried Nettles leaf, providing four drams of dried Cowslip, bring the two quarts of water to a boil, removing the two quarts of water from heat, adding the four drams of White Willow bark, adding the four drams of German Chamomile, adding the four drams of Parsley, adding the four drams of Nettles leaf, adding the four drams of Cowslip thus forming a mixture, stirring the mixture, covering the mixture tightly, allowing the mixture to steep for ten minutes, uncovering the mixture, stirring the mixture, covering the mixture tightly, allowing the mixture to steep for ten minutes, uncovering the mixture, straining the mixture into a drinking receptacle, allowing the mixture to cool, refrigerating the mixture, drinking 8 ounces of the mixture in the morning and evening and repeating twice a day drinking for six to eight weeks, and if symptoms persist continuing the drinking step for another six to eight weeks.

This herbal tea is beneficial for arthritis, both osteo and rheumatoid, digestion and sleep. The ingredients are White Willow bark, German Chamomile, Parsley, Nettles Leaf, and Cowslip which is also known as primula veris. The synergistic effect of this specific combination of natural herbs, consumed pursuant to the included regimen regularly over a several month period, is beneficial to joint health, as well as digestive tract health and insomnia.

The tea is prepared by boiling two quarts of water then removing it to the heat. Add four drams, dry measure, of each of the herbs listed above, stir well. Cover tightly and steep for ten minutes. Uncover and stir well again. Cover tightly and steep for another ten minutes. Strain into a glass or ceramic container. Cool and then refrigerate.

The regimen consists of drinking one cup, 8 ounces, of the tea teach morning upon rising and each evening before retiring for six to eight weeks until arthritis pain is relieved. The regimen must be followed strictly. If partial relief is achieved after 8 weeks, continue drinking the tea until relief is complete.

Test subjects reported that nothing else restored joint health to the extent of this tea. Consistently reported additional benefits included improved digestive function and improved sleep.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United is as follows:

1. A restorative tea system to combat osteo and rheumatoid arthritis, digestive tract disorders, and sleep disorders comprising, in combination:

two quarts of heated water;

four drams of dried White Willow bark;

four drams of dried German Chamomile;

four drams of dried Parsley;

four drams of dried Nettles leaf; and four drams of dried Cowslip also known as primula veris.

2. A restorative tea system comprising, in combination:

one part of White Willow bark;

one part of German Chamomile;

one part of Parsley;

one part of Nettles leaf; and one part of primula veris.

3. A method of brewing a restorative tea for combating osteo and rheumatoid arthritis, digestive tract disorders, and sleep disorders including:

providing two quarts of water;

providing four drams of dried White Willow bark;

providing four drams of dried German Chamomile;

providing four drams of dried Parsley;

providing four drams of dried Nettles leaf;

providing four drams of dried Cowslip;

bringing the two quarts of water to a boil;

removing the two quarts of water from heat;

adding the four drams of White Willow bark;

adding the four drams of German Chamomile;

adding the four drams of Parsley;

adding the four drams of Nettles leaf;

adding the four drams of Cowslip thus forming a mixture;

stirring the mixture;

covering the mixture tightly;

allowing the mixture to steep for ten minutes;

uncovering the mixture;

stirring the mixture;

covering the mixture tightly;

allowing the mixture to steep for ten minutes;

uncovering the mixture;

straining the mixture into a drinking receptacle;

allowing the mixture to cool;

refrigerating the mixture;

drinking 8 ounces of the mixture in the morning and evening and repeating twice a day for six to eight weeks; and if symptoms persist continuing the drinking step for another six to eight weeks.

4. A method of brewing restorative tea including:

providing water;

providing one part of White Willow bark;

providing one part of German Chamomile;

providing one part of Parsley;

providing one part of Nettles leaf;

providing one part of Cowslip;

bringing the water to a boil;

removing the water from heat;

adding the White Willow bark, German Chamomile, Parsley, Nettles leaf, and primula veris thus forming a mixture;

stirring the mixture;

covering the mixture tightly;

allowing the mixture to steep for ten minutes;

uncovering the mixture;

stirring the mixture;

covering the mixture tightly;

allowing the mixture to steep for ten minutes;

uncovering the mixture;

straining the mixture into a drinking receptacle; and allowing the mixture to cool.

\* \* \* \* \*